United States Patent
Alsiddiky et al.

(10) Patent No.: US 10,507,014 B1
(45) Date of Patent: Dec. 17, 2019

(54) SURGICAL RETRACTOR

(71) Applicant: KING SAUD UNIVERSITY, Riyadh (SA)

(72) Inventors: Abdulmonem Alsiddiky, Riyadh (SA); Raheef Mohamed Alatassi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/987,674

(22) Filed: May 23, 2018

(51) Int. Cl.
*A61B 17/02* (2006.01)
*A61M 1/00* (2006.01)

(52) U.S. Cl.
CPC ........... *A61B 17/02* (2013.01); *A61M 1/0086* (2014.02); *A61B 2217/005* (2013.01)

(58) Field of Classification Search
CPC ... A61B 17/02; A61B 17/0218; A61M 1/0086
USPC .......................................... 600/201, 205, 210
See application file for complete search history.

(56) References Cited

U.S. PATENT DOCUMENTS

| | | | |
|---|---|---|---|
| 5,123,403 A | 6/1992 | Lavyne | |
| D622,381 S | 8/2010 | Hajarian et al. | |
| 8,518,014 B2 * | 8/2013 | Fassuliotis | A61M 1/008 604/523 |
| D704,835 S | 5/2014 | Hajarian et al. | |
| D718,856 S | 12/2014 | Altschuler | |
| 8,992,524 B1 * | 3/2015 | Ellman | A61B 18/148 606/41 |
| 9,533,080 B1 | 1/2017 | Carrier | |
| 2006/0200183 A1 * | 9/2006 | Gardocki | A61B 17/0218 606/190 |
| 2007/0060793 A1 | 3/2007 | DeGould | |
| 2009/0069802 A1 * | 3/2009 | Garito | A61B 18/14 606/45 |
| 2012/0029294 A1 * | 2/2012 | Smith | A61B 17/3421 600/205 |
| 2012/0078059 A1 | 3/2012 | Perez-Cruet et al. | |
| 2013/0281784 A1 | 10/2013 | Ray | |
| 2014/0257039 A1 | 9/2014 | Feldman | |

FOREIGN PATENT DOCUMENTS

| | | |
|---|---|---|
| CN | 201333250 Y | 10/2009 |
| CN | 201350085 Y | 11/2009 |
| CN | 203749888 U | 8/2014 |
| CN | 204233593 U | 4/2015 |
| KR | 20160047689 A | 5/2016 |

* cited by examiner

*Primary Examiner* — Si Ming Ku
(74) *Attorney, Agent, or Firm* — Richard C. Litman; Nath, Goldberg & Meyer

(57) ABSTRACT

A surgical retractor includes an elongated body having a handle portion, a retractor arm connected to the handle portion, a retractor tip at an end of the retractor arm, and a suction connector extending through a wall of the handle portion. An inner retractor cavity extends within the retractor from the suction connector to an opening at an outer surface of the retractor tip. The suction connector can be selectively connected to an external suction or vacuum device. The surgical retractor can be used to hold and/or move tissues to expose a surgical field and to collect blood, fluid, smoke, and/or surgical debris from a surgical field.

5 Claims, 3 Drawing Sheets

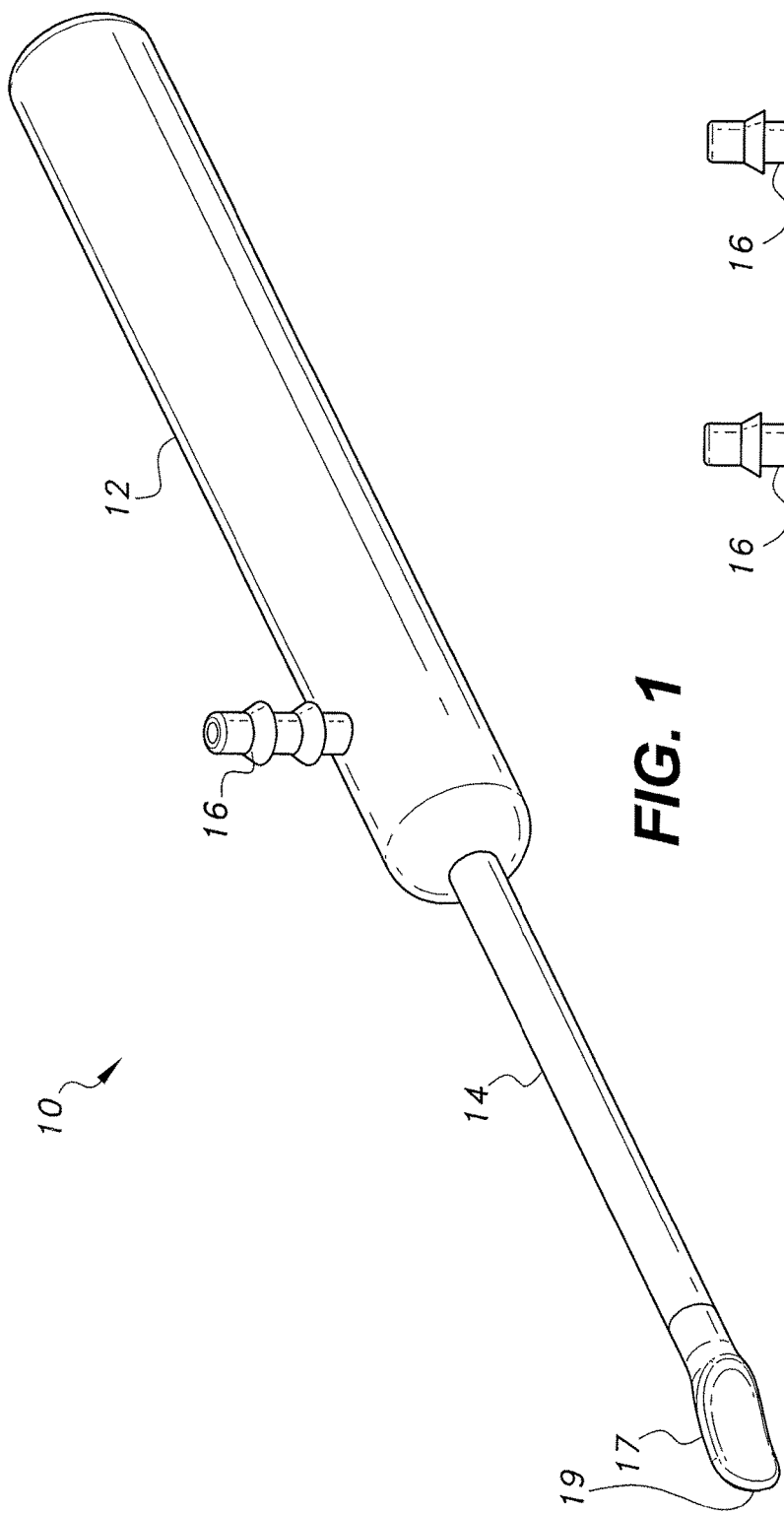
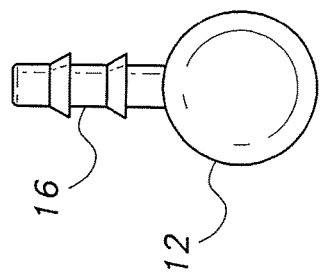
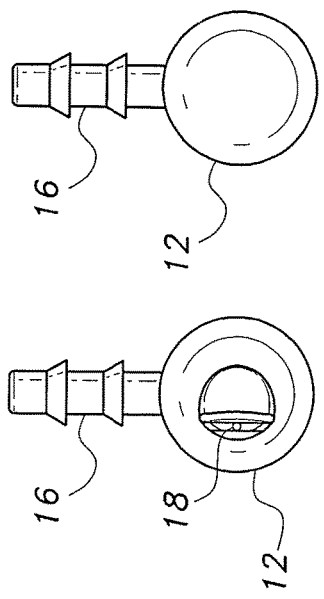
FIG. 1
FIG. 3
FIG. 2

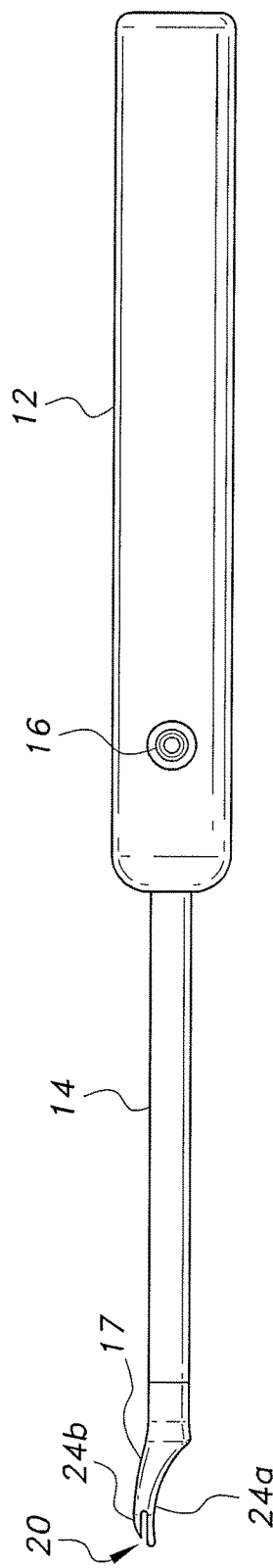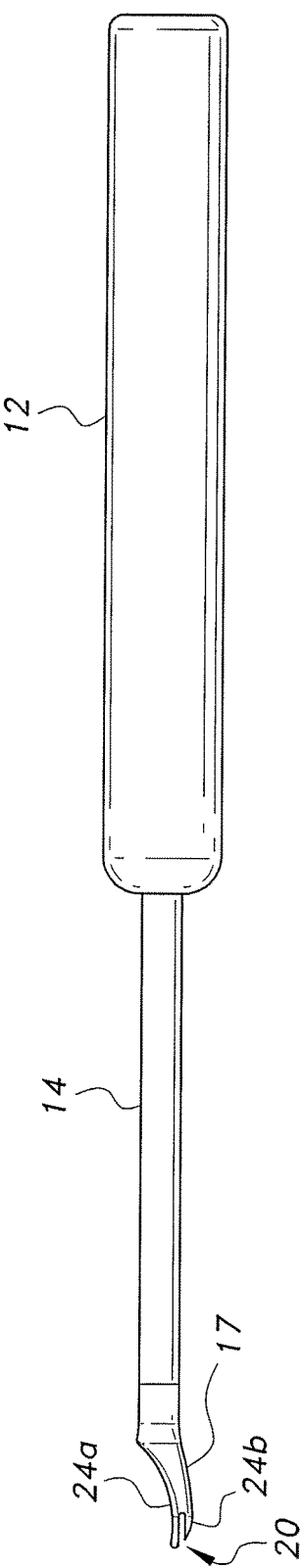

SURGICAL RETRACTOR

BACKGROUND

1. Field

The disclosure of the present patent application relates to a surgical instrument, and particularly, to a surgical retractor with suction for orthopedic surgery.

2. Description of the Related Art

Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site.

In orthopedic surgeries, an orthopedic surgical retractor, e.g., a cobb retractor, is typically used to retract, hold, and reposition skin, muscle, and/or other tissue to expose a surgical field. Retraction is generally accompanied by operation of a separate suction device by an assistant. The suction device is used to collect fluid, smoke, and/or surgical debris from the surgical field.

Often times, operation of a surgical retractor and a separate suction device can be cumbersome. Additionally, the assistant operating the suction device can hamper free movement of the operator and/or block the operator's view of the surgical field.

Thus, a surgical retractor with suction solving the aforementioned problems is desired.

SUMMARY

A surgical retractor includes a generally elongated or cylindrical body having a handle portion, a retractor arm connected to the handle portion, a retractor tip at an end of the retractor arm, and a suction connector extending through a side of the handle portion. An inner retractor cavity extends within the retractor from the suction connector to an opening at an outer surface of the retractor tip. The suction connector can be selectively connected to an external suction or vacuum device. The surgical retractor can be used to hold and/or move skin, muscle, and soft tissues to expose a surgical field and to collect blood, fluid, smoke, and/or surgical debris from the surgical field.

These and other features of the present disclosure will become readily apparent upon further review of the following specification and drawings.

BRIEF DESCRIPTION OF THE DRAWINGS

FIG. 1 is a perspective view of a surgical retractor with suction.

FIG. 2 is a front view of the surgical retractor with suction.

FIG. 3 is a rear view of the surgical retractor with suction.

FIG. 6 is a top view of the surgical retractor with suction.

FIG. 7 is a bottom view of the surgical retractor with suction.

Similar reference characters denote corresponding features consistently throughout the attached drawings.

DETAILED DESCRIPTION OF THE PREFERRED EMBODIMENTS

A surgical retractor or "cobb" retractor 10, according to the present teachings, is a surgical instrument that can be used during a surgical procedure to move or space apart skin, muscle, and/or other tissue that block a surgical field. The surgical retractor 10 is particularly useful for orthopedic surgical procedures, such as spine, arthroplasty, and other orthopedic surgeries.

Figure 4:
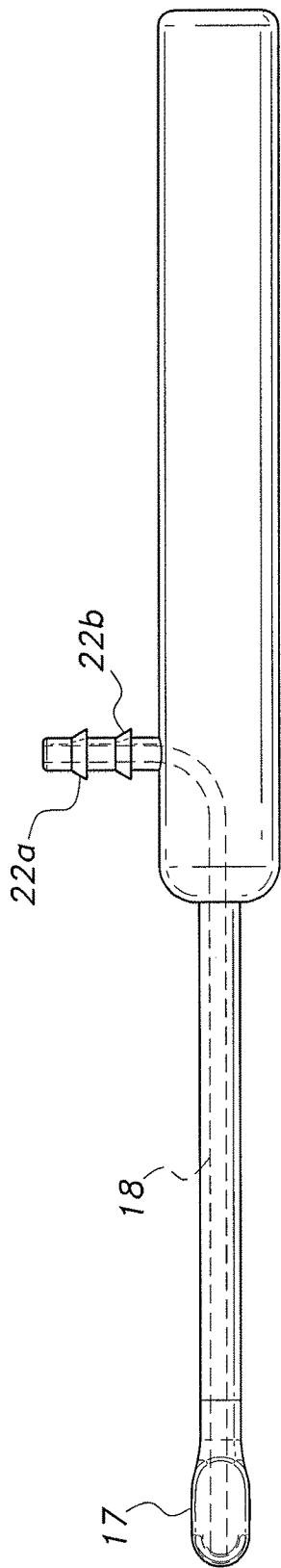
FIG. 4 is a first side view of the surgical retractor with suction, showing the internal cavity with dashed lines.
Figure 5:
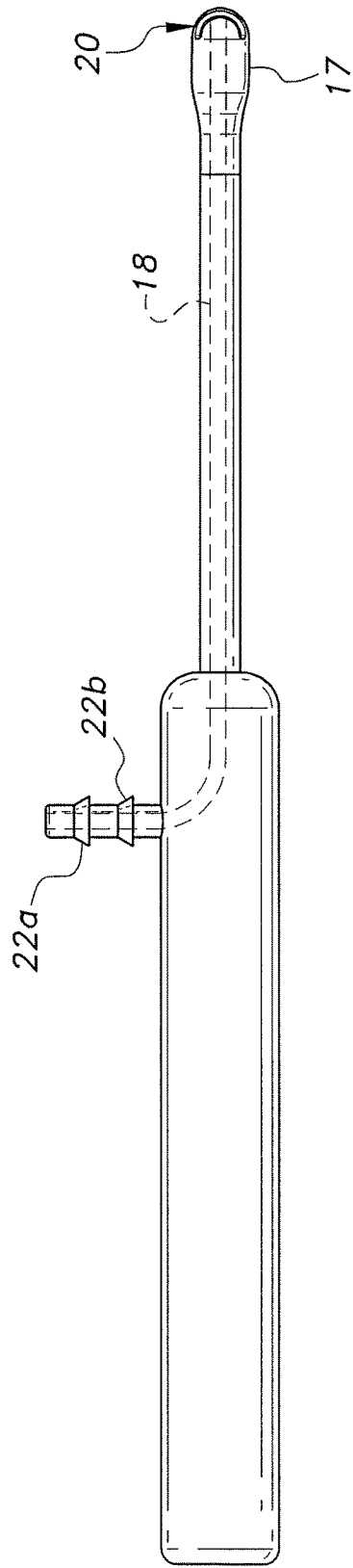
FIG. 5 is a second side view of the surgical retractor with suction, showing the internal cavity with dashed lines and the opening at the outer surface of the retractor tip.

As shown in FIGS. 1-7, the surgical retractor 10 includes a generally elongated or cylindrical body having a handle portion 12, a retractor arm 14 connected to the handle portion 12, a retractor tip 17 at an end of the retractor arm 14, and a suction connector 16 extending through a side of the handle portion 12. An inner retractor cavity 18 (FIGS. 4-5) extends within the retractor from the suction connector 16 to an opening 20 at an outer surface of the retractor tip 17. The suction connector 16 can be selectively connected to an external suction or vacuum device. The surgical retractor 10 can be used to hold and/or move skin, muscle, and soft tissues to expose a surgical field and collect blood, fluid, smoke, and/or surgical debris from a surgical field.

The retractor arm 14 can be generally linear or elongated. A diameter of the retractor arm 14 can be tapered, e.g., the diameter of the arm 14 proximate the handle portion 12 can be greater than the diameter of the arm 14 proximate the retractor tip 17. The handle portion 12 can have a larger diameter than the retractor arm 14. The suction connector 16 can extend normal to the handle portion 12. For example, the suction connector 16 can extend from a peripheral sidewall of the handle portion 12. The suction connector 16 can be disposed closer to the retractor arm 14 than the free end of the handle portion 12. In this manner, the suction connector 16 does not compromise the surgical field, while being easily accessible to the operator. The suction connector 16 can include threads or ridges 22a, 22b to facilitate connection with an external suction device.

The retractor tip 17 can include a generally flat, inner surface 24a and a curved or convex outer surface 24b. The retractor tip 17 can further include a wide, curved edge 19. The opening 20 defined in the outer surface 24b of the tip 17 extends to the inner cavity 18. The opening 20 can be semi-circular. The inner cavity 18 can include a soft curve to connect the tip to the suction connector 16. Preferably, the inner cavity 18 is devoid of sharp angles or bends to prevent or minimize the occurrence of blockages as materials are suctioned through the tube.

The retractor 10 can be formed from any suitable, surgical grade material. For example, the retractor 10 can be formed from a metal material, such as, stainless steel, titanium, or tungsten carbide. Preferably, the metal material is corrosion resistant, e.g., inox steel. The retractor 10 can be formed from a disposable material, such as a disposable, plastic material. The retractor 10 can have any suitable dimensions, e.g., a length of about 24 centimeters. According to some embodiments, the retractor 10 can be configured to have an adjustable length.

The retractor 10 can be used during a surgical procedure to both retract tissue and collect debris from a surgery site. Accordingly, use of the retractor 10 obviates the need for carrying out these functions using two separate instruments, e.g., a conventional retractor and a conventional suction device. As the retractor 10 alone can perform functions which previously necessitated the use of two separate instruments, an operator can utilize cautery instruments to cut tissue with greater ease than was previously possible. Further, an operator using the retractor 10 will not have to rely on the assistance of another individual to operate a separate suction device.

It is to be understood that the surgical retractor with suction for orthopedic surgery is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A surgical retractor with suction, consisting of:
   an elongated handle portion, the handle portion having a longitudinal axis and a peripheral sidewall;
   an elongated retractor arm connected to the handle portion, the retractor arm having a longitudinal axis aligned with the longitudinal axis of the handle portion and define a common vertical plane;
   a retractor tip extending from an end of the retractor arm, the retractor tip having an outer convex surface, an opposing inner flat surface, a smooth curved edge, and a semi-circular opening defined at the outer convex surface thereof and substantially coextensive with the curved edge, wherein the retractor tip defines a substantially horizontal plane perpendicular to the common vertical plane;
   a suction connector extending upwardly from and through the peripheral sidewall of the handle portion for selective connection to an external suction device, wherein the suction connector is located adjacent the connection to the elongated retractor arm thereby locating it closer to the retractor arm than a free end of the handle portion, further wherein the suction connector has a longitudinal axis perpendicular to the common vertical plane and substantially parallel to the horizontal plane of the retractor tip; and
   an inner retractor cavity extending within the retractor arm from the suction connector to the opening at the retractor tip, wherein the portion of the retractor cavity extending between the suction connector and the retractor arm is arcuately shaped and the remaining portion of the retractor cavity is straight.

2. The surgical retractor according to claim 1, wherein the handle portion comprises a larger diameter than the retractor arm.

3. The surgical retractor according to claim 1, wherein a length of the surgical retractor is 24 centimeters.

4. The surgical retractor according to claim 1, wherein the surgical retractor is formed from a metal material.

5. The surgical retractor according to claim 1, wherein the surgical retractor is formed from a plastic material.

* * * * *